(12) United States Patent
Obinata et al.

(10) Patent No.: US 7,707,001 B2
(45) Date of Patent: Apr. 27, 2010

(54) CONTROL OF OBJECT OPERATING FORCE, OBJECT GRIPPING FORCE AND ROBOT HANDS

(75) Inventors: Goro Obinata, Aichi (JP); Kiyoshi Oka, Ibaraki (JP); Hiroki Miura, Aichi (JP); Nobuhiko Moriyama, Aichi (JP)

(73) Assignee: Nagoya Industrial Science Research Institute, Aichi (JP)

( * ) Notice: Subject to any disclaimer, the term of this patent is extended or adjusted under 35 U.S.C. 154(b) by 435 days.

(21) Appl. No.: 10/592,243

(22) PCT Filed: Mar. 4, 2005

(86) PCT No.: PCT/JP2005/004259

§ 371 (c)(1),
(2), (4) Date: Aug. 17, 2007

(87) PCT Pub. No.: WO2005/085785

PCT Pub. Date: Sep. 15, 2005

(65) Prior Publication Data

US 2008/0027582 A1    Jan. 31, 2008

(30) Foreign Application Priority Data

Mar. 9, 2004   (JP)   ............................. 2004-066401

(51) Int. Cl.
*G01L 1/00*     (2006.01)
*G06F 17/40*    (2006.01)

(52) U.S. Cl. .......................... 702/127; 702/40; 702/41; 356/32

(58) Field of Classification Search ................. 702/127, 702/40, 41
See application file for complete search history.

(56) References Cited

U.S. PATENT DOCUMENTS

| 4,599,908 | A  | * | 7/1986  | Sheridan et al. ........ 73/862.046 |
| 7,460,964 | B2 | * | 12/2008 | Mizota et al. .................. 702/41 |
| 2003/0178556 | A1 | * | 9/2003 | Tachi et al. ............ 250/227.11 |

(Continued)

FOREIGN PATENT DOCUMENTS

GB    2351554 A    *    1/2001

(Continued)

OTHER PUBLICATIONS

Katsuto Kamiyama et al., Development of a Vision-based Tactile Sensor, IEEE Transactions on Semiconductor Manufacturing, vol. 123, No. 1, 2003, pp. 16-21.

(Continued)

*Primary Examiner*—Hal D Wachsman
(74) *Attorney, Agent, or Firm*—Lahive & Cockfield, LLP; Anthony A. Laurentano

(57) ABSTRACT

An optical tactile sensor has a touch pad and a CCD camera for imaging behavior of the touch pad. A CPU processes image information from the CCD camera, extracts information on the size, shape, and center of gravity of a contact region, and extracts information on the size of a fixation region. The CPU obtains a normal force from the size of the contact region, obtains a tangential force from the shape of the contact region and the center of gravity of the contact region, and obtains a friction coefficient from the ratio of the size of the fixation region to the size of the contact region.

11 Claims, 7 Drawing Sheets

U.S. PATENT DOCUMENTS

2007/0043508 A1* 2/2007 Mizota et al. ................ 702/19
2008/0245955 A1* 10/2008 Tachi et al. ................. 250/221

FOREIGN PATENT DOCUMENTS

| JP | 3-47021 | 7/1991 |
| JP | 7-26805 | 3/1995 |
| JP | 11-304602 | 11/1999 |
| JP | 2000-254884 | 9/2000 |
| JP | 2005-114715 | 4/2005 |
| WO | WO 02/18893 A1 | 3/2002 |

OTHER PUBLICATIONS

Shinichi Hiromitsu et al., Stick/slip Distribution on the Fingerpad and Response to Tactile Receptors when Human Grasp an Object, Transaction of the Japan Society of Mechanical Engineers, vol. 68, No. 667 (20020325) pp. 914-919, ISSN: 03875024, Mar. 2002.

* cited by examiner

CONTROL OF OBJECT OPERATING FORCE, OBJECT GRIPPING FORCE AND ROBOT HANDS

RELATED APPLICATIONS

This application is a 35 U.S.C. 371 national stage filing of International Application No. PCT/JP2005/004259, filed 4 Mar. 2005, which claims priority to Japan Patent Application No. 2004-066401 filed on 9 Mar. 2004 in Japan. The contents of the aforementioned applications are hereby incorporated by reference.

BACKGROUND OF THE INVENTION

The present invention relates to optical tactile sensors, sensing methods using optical tactile sensors, sensing systems, methods and apparatuses for controlling object operating force, apparatuses for controlling object gripping force, and robot hands.

Although a society where humans and humanoid robots coexist side by side is becoming more realistic, there remain a number of problems to be solved first. While improving the maneuverability and the intelligence of robots is of great importance for this purpose, improving the technology for allowing communication between humans and robots is also thought to provide a shortcut to a society where humans and robots can coexist.

What is central to such communication technology is remote control of robots that perform tasks under human direction. In the field of remotely controlling robots, a key technology for smoothly executing tasks includes sensing tactile information with tactile sensors. One exemplary technology being contemplated is that of sensing the weight and the coefficient of friction of the object (to be handled) and adjusting the gripping force of the robot hand based on the weight and the coefficient of friction sensed. Such gripping force adjustment is expected to allow the robot to grip objects without damaging or dropping them.

Also contemplated has been application of the same principle for sensing an object's friction coefficient (slip) to a tactile sensor as that used in human fingertips so as to facilitate sensing the slip by the sensor (see, for example, Hiromitsu, S. and Maeno, T.: "Stick/slip Distribution on the Fingerpad and Response of Tactile Receptors when Human Grasp an Object," The Japan Society of Mechanical Engineers, Vol. 68, No. 667 C: 914-919(March 2002). This document discloses the principle of detecting the slip (coefficient of friction) of an object by extracting a "fixed region" and a "slip region" within the region of contact between the object and the tactile portion of the robot hand.

A conventional sensor of this type that employs this principle includes a mechanical tactile sensor with a plurality of strain gauges arranged within elastic curved bodies for measuring the pressure distribution or the distribution of distortion within the elastic bodies based on the output of each strain gauge so as to determine the slipperiness and fixedness of the object (see, for example, Japanese Published Unexamined Patent Application No. 2000-254884).

Another type of a conventional sensor is an optical tactile sensor that captures the deformation of a clear elastic object with imaging means, such as a CCD camera. This can be achieved, for example, by embedding layers of spherical markers in a clear elastic body shaped into a rectangular parallelepiped and measuring the displacement of each marker with a CCD camera so as to measure the three-dimensional force vector and torque that occur approximately on the contact region (see, for example, Japanese Published Unexamined Patent Application No. 2000-523568 and Kamiyama, K., Kajimoto, H., Inami, M., Kawakami, N., and Tachi, S.: "Development of A Vision-based Tactile Sensor," IEEJ Trans, SM, Vol. 123.No. 1, 16-22(2003)).

One problem associated with the mechanical tactile sensor is its insufficient durability, since it performs sensing by allowing the strain gauges to be deformed. Moreover, as a plurality of strain gauges need to be arranged within an elastic body, the manufacturing of the sensor may become complicated or the wiring may become difficult.

On the other hand, in the above-described optical tactile sensor, as the surface of contact with the clear object (to be gripped) is flat, it is difficult to detect the coefficient of friction between the object and the sensor's tactile portion. Furthermore, providing curvature for the above-mentioned surfaces of contact, if attempted, would be extremely difficult.

Additionally, a finger-like tactile sensor has been proposed. However, such a finger-like sensor can only measure the state of contact and the contact pressure, thus being incapable of simultaneously measuring multi-dimensional mechanical quantities, including the coefficient of friction.

A combination of different types of tactile sensors, i.e., mechanical tactile sensors and optical tactile sensors, has been proposed as a means for measuring multi-dimensional mechanical quantities (see Hiromitsu, S. and Maeno, T.: "Stick/slip Distribution on the Fingerpad and Response of Tactile Receptors when Human Grasp an Object," The Japanese Society of Mechanical Engineers, Vol. 68, No. 667 C: 914-919(March 2002)). However, such a sensing means would not be amenable to size-reduction since it requires two different types of sensors.

One object of the present invention, which has been made in view of the foregoing problems, is to provide an optical tactile sensor that can be easily manufactured and reduced in size. Another object of the present invention is to provide a sensing method and system, a method and apparatus for controlling object operating force, an apparatus for controlling object gripping force, and a robot all equipped with one type of optical tactile sensors which simultaneously sense different mechanical quantities in an exemplary embodiment.

SUMMARY OF THE INVENTION

The first embodiment of the present invention, which has been made to solve the above-identified problems, provides an optical tactile sensor characterized by comprising a tactile portion made of an optically transparent elastic body which includes a convex curved surface and has a marker portion disposed on the convex curved surface, and imaging means for imaging behavior of the marker portion while an object is in contact with the convex curved portion.

Therefore, according to the first embodiment, since the behavior of the optically transparent elastic body is captured as image data by the imaging means, a large amount of data can be processed with a relatively small and simple structure.

Accordingly, even different types of mechanical quantities (for example, a normal force, a tangential force, a coefficient of friction, and a torque) can be measured simultaneously without using a combination of different types of sensors. This provides for easy manufacture of the optical tactile sensor. Moreover, the marker portion or a plurality of strain gauges need not be disposed or arranged inside the optically transparent elastic body, thus facilitating the manufacture of the optical tactile sensor.

The convex curved surface is the part of the tactile portion most susceptible to deformation when the portion comes into contact with an object. The amount of deformation becomes progressively smaller from the convex curved surface into the inside of the tactile portion. Therefore, the marker portion of this embodiment, being disposed on the convex curved surface, tends to exhibit greater deformation compared with a marker portion formed within the tactile portion. This allows for accurate determination of the forces acting on the tactile portion when the imaging means images the deformation of the marker portion. In other words, the deformation of the optically transparent elastic body can be sensed more accurately with this embodiment than with the method for sensing the deformation that occurs inside the elastic body.

Although the preferred material for the optically transparent elastic body is a silicone resin, such as silicone rubber, the elastic body may be made of any other suitable optically transparent material, such as other types of rubber and elastomer. Furthermore, the optically transparent elastic body may be clear or translucent.

In addition, the marker portion should be disposed only on the convex curved surface of the optically transparent elastic body rather than inside the elastic body. In other words, the marker portion is preferably disposed in a single layer on the convex curved surface. This is because a marker portion disposed inside the optically transparent elastic body, especially if it is in a plurality of layers, would make the manufacture of the optical tactile sensor difficult. The marker portion may be provided either by attaching (e.g., applying, pasting, or printing) a separate material to the optically transparent elastic body or shaping the elastic body without using a separate material. The latter is the preferred method of forming the marker portion. This is because a marker formed by attaching a separate material to the optically transparent elastic material may be dislodged by an object coming into contact with the convex curved surface. Another reason for the preference of the latter method is that attaching a separate material to the optically transparent elastic material may add to the manufacturing cost of the optical tactile sensor. The marker portion provided on the optically transparent elastic material may take various forms, including grooves, ridges, protrusions, and depressions. Furthermore, the marker portion may be either colorless or colored.

The imaging means preferably employs a camera that generates image data as electrical signals. A particularly preferred imaging means is a digital camera. Examples of such a digital camera include a CCD camera and digital camera using a CMOS image sensor.

Preferably, the marker portion comprises a plurality of grooves or ridges arranged in a grid pattern. The marker portion, if it includes a plurality of grooves or ridges arranged in a grid pattern, facilitates recognition of its deformation caused by forces acting on the tactile portion.

This in turn facilitates determination of the forces acting on the tactile portion when the imaging means images the deformation of the marker portion.

Preferably, the tactile portion is formed by providing a mold having a plurality of molding grooves or ridges on its molding surface and allowing material for an elastic body in an uncured state to be cured while in contact with the molding surface. Such molding grooves form ridges and such molding ridges forms grooves concurrently with the formation of the entire tactile portion. This provides for easy manufacture of the tactile portion even though the tactile portion has a convex curved surface. Moreover, this eliminates the need for the step of attaching a separate material to the optically transparent elastic material, thus reducing the entire manufacturing cost of the elastic material.

The second embodiment of the present invention provides a method for sensing different types of mechanical quantities by using an optical tactile sensor that has a tactile portion made of an optically transparent elastic body and imaging means for imaging behavior of the part of the tactile portion with which an object comes into contact, the method characterized by comprising the steps of: extracting information on the size, shape, and center of gravity of a contact region that occurs between the object and the tactile portion, and extracting information on the size of a fixed region between the object and the tactile portion that occurs within the contact region, both by processing image data from the imaging means; obtaining a normal force from the size of the contact region; obtaining a tangential force from the shape of the contact region and the center of gravity of the contact region; and obtaining a coefficient of friction from the ratio of the size of the fixed region to that of the contact region.

According to the second embodiment of the present invention, once image data from the imaging means is image processed, information about the size, shape, and center of gravity of the contact region as well as the size of the fixed region is extracted. Then a normal force, a tangential force, and a coefficient of friction are obtained based on that information. In other words, a single type of sensor may simultaneously measure different types of mechanical quantities.

The third embodiment of the present invention provides a sensing system characterized by comprising: an optical tactile sensor that has a tactile portion made of an optically transparent elastic body and imaging means for imaging behavior of the part of the tactile portion with which an object comes into contact; information extracting means for extracting information on the size, shape, and center of gravity of a contact region that occurs between the object and the tactile portion and for extracting information on the size of a fixed region between the object and the tactile portion that occurs within the contact region, both by processing image data from the imaging means; and mechanical quantity measuring means which, in an exemplary embodiment, obtain a normal force from the size of the contact region, obtain a tangential force from the shape of the contact region and the center of gravity of the contact region, and obtain a coefficient of friction from the ratio of the size of the fixed region to that of the contact region.

According to the third embodiment of the present invention, once image data from the imaging means is image processed, the information extracting means extracts information about the size, shape, and center of gravity of the contact region as well as the size of the fixed region. Subsequently, the mechanical quantity measuring means measures a normal force, a tangential force, and a coefficient of friction based on that information. In other words, a single type of sensor may simultaneously measure different types of mechanical quantities.

In the third embodiment of the present invention, it is preferable to have a marker portion disposed on the part of the tactile portion surface with which the object comes into contact with, whereas the imaging means images behavior of the marker portion while the object is in contact with the tactile portion. It is also preferable that the information extracting means extracts information about deformation of the marker portion by image processing image data from the imaging means, whereas the mechanical quantities measuring means obtains a torque from the information about the deformation of the marker portion. According to this construction, the marker portion is disposed on the part of the tactile portion surface that is most susceptible to deformation, causing the marker portion to deform almost as soon as torque starts acting on the tactile portion. Accordingly, the degree of deformation of the marker portion approximately corresponds to that of the tactile portion. Not only can one type of sensor simultaneously measure different types of mechanical quantities (a normal force, a tangential force, and coefficient of friction), but also it can accurately measure a torque by imaging the deformation of the marker portion with the imaging means.

The fourth embodiment of the present invention provides a method for controlling forces for operating an object by using an optical tactile sensor that has a tactile portion made of an optically transparent elastic body and imaging means for imaging behavior of the part of the tactile portion with which an object comes into contact, the method characterized by comprising the steps of: extracting information on the size, shape, and center of gravity of a contact region that occurs between the object and the tactile portion, and extracting information on the size of a fixed region between the object and the tactile portion that occurs within the contact region, both by processing image data from the imaging means; obtaining a normal force from the size of the contact region, obtaining a tangential force from the shape of the contact region and the center of gravity of the contact region, and obtaining a coefficient of friction from the ratio of the size of the fixed region to that of the contact region; calculating an operating force suitable for application to the object based on the different types of mechanical quantities obtained by the mechanical quantity measuring means; and performing control to approximate the different types of mechanical quantities to the suitable operating force calculated.

According to the fourth embodiment of the present invention, once image data from the imaging means is image processed, information about the size, shape, and center of gravity of the contact region as well as the size of the fixed region is extracted. Then a normal force, a tangential force, and a coefficient of friction are obtained based on that information. In other words, a single type of sensor may simultaneously measure different types of mechanical quantities. Adjustments can then be made based on the measured mechanical quantities so as to produce gripping force suitable for application to the object. This achieves desired control by applying suitable force to the object. The term "operating force" refers to the force to push, rotate, and/or grip an object with the tactile portion in contact with the object.

The fifth embodiment of the present invention provides an apparatus for controlling forces to operate an object, characterized by comprising: a sensor support; an actuator for driving the sensor support; an optical tactile sensor that has a tactile portion made of an optically transparent elastic body and imaging means for imaging behavior of the part of the tactile portion that comes into contact with an object, the optical tactile sensor being supported by the sensor support; information extracting means for extracting information on the size, shape, and center of gravity of a contact region that occurs between the object and the tactile portion and for extracting information on the size of a fixed region between the object and the tactile portion that occurs within the contact region, both by processing image data from the imaging means; mechanical quantity measuring means which, in an exemplary embodiment, obtain a normal force from the size of the contact region, obtain a tangential force from the shape of the contact region and the center of gravity of the contact region, and obtain a coefficient of friction from the ratio of the size of the fixed region to that of the contact region; operating force calculating means for calculating an operating force suitable for application to the object based on the different types of mechanical quantities obtained by the mechanical quantity measuring means; and actuator drive control means for performing feedback control of the actuator so as to drive the sensor support with the suitable operating force calculated by the operating force calculating means.

According to the fifth embodiment of the present invention, once image data from the imaging means is image processed, the information extracting means extracts information about the size, shape, and center of gravity of the contact region as well as the size of the fixed region. Subsequently, the mechanical quantity measuring means measures a normal force, a tangential force, and a coefficient of friction based on that information. In other words, a single type of sensor may simultaneously measure different types of mechanical quantities. The operating force calculating means can then calculate an operating force suitable for application to the object based on the measured mechanical quantities. This achieves desired control by applying suitable force to the object.

Moreover, even if the appropriate operating force to be exerted on the object changes during the operation, the feedback control performed by the actuator drive control means continues appropriate operation on the object.

The sixth embodiment of the present invention provides an apparatus for controlling forces to grip an object, the apparatus characterized by comprising: a sensor support; an actuator for driving the sensor support; an optical tactile sensor that has a tactile portion made of an optically transparent elastic body and imaging means for imaging behavior of the part of the tactile portion that comes into contact with an object, the optical tactile sensor being supported by the sensor support; information extracting means for extracting information on the size, shape, and center of gravity of a contact region that occurs between the object and the tactile portion and for extracting information on the size of a fixed region between the object and the tactile portion that occurs within the contact region, both by processing image data from the imaging means; mechanical quantity measuring means which, in an exemplary embodiment, obtain a normal force from the size of the contact region, obtain a tangential force from the shape of the contact region and the center of gravity of the contact region, and obtain a coefficient of friction from the ratio of the size of the fixed region to that of the contact region; gripping force calculating means for calculating a gripping force suitable for application to the object based on the different types of mechanical quantities obtained by the mechanical quantity measuring means; and actuator drive control means for performing feedback control of the actuator so as to drive the sensor support with the suitable gripping force calculated by the gripping force calculating means.

According to the sixth embodiment of the present invention, once image data from the imaging means is image processed, the information extracting means extracts information about the size, shape, and center of gravity of the contact region as well as the size of the fixed region. Subsequently, the mechanical quantity measuring means measures a normal force, a tangential force, and a coefficient of friction based on that information. In other words, a single type of sensor may simultaneously measure different types of mechanical quantities. The operating force calculating means can then calculate a gripping force suitable for application to the object based on the measured mechanical quantities. This allows an object to be gripped without being damaged or dropped. Moreover, even if the appropriate gripping force to be exerted on the object changes during the operation, the feedback control performed by the actuator drive control means maintains the grip on the object without damaging or dropping it.

The seventh embodiment of the present invention provides a robot hand characterized by comprising: a plurality of fingers; actuators for driving the plurality of fingers; at least one optical tactile sensor that has a tactile portion made of an optically transparent elastic body and imaging means for imaging behavior of the part of the tactile portion that comes into contact with an object, each of the at least one optical tactile sensor being supported by a distal end of one of the plurality of fingers; information extracting means for extracting information on the size, shape, and center of gravity of a contact region that occurs between the object and the tactile portion and for extracting information on the size of a fixed region between the object and the tactile portion that occurs within the contact region, both by processing image data from the imaging means; mechanical quantity measuring means which, in an exemplary embodiment, obtain a normal force from the size of the contact region, obtain a tangential force from the shape of the contact region and the center of gravity of the contact region, and obtain a coefficient of friction from the ratio of the size of the fixed region to that of the contact region; gripping force calculating means for calculating a gripping force suitable for application to the object based on the different types of mechanical quantities obtained by the mechanical quantity measuring means; and actuator drive control means for performing feedback control of the actuators so as to drive the plurality of fingers with the suitable gripping force calculated by the gripping force calculating means.

According to the seventh embodiment of the present invention, once image data from the imaging means is image processed, the information extracting means extracts information about the size, shape, and center of gravity of the contact region as well as the size of the fixed region. Subsequently, the mechanical quantity measuring means measures a normal force, a tangential force, and a coefficient of friction based on that information. In other words, a single type of sensor may simultaneously measure different types of mechanical quantities. The operating force calculating means can then calculate a gripping force suitable for application to the object based on the measured mechanical quantities. This allows an object to be gripped by a plurality of fingers without being damaged or being permitted to slip through the fingers. This facilitates the creation of a humanoid robot with a robot hand having functionality closer to that of the human hand.

Moreover, even if the appropriate gripping force to be exerted on the object changes during the operation, the feedback control performed by the actuator drive control means maintains the grip on the object without damaging it or letting it slip through the fingers.

BRIEF DESCRIPTION OF THE ILLUSTRATED DRAWINGS

DETAILED DESCRIPTION OF THE INVENTION

A multi-dimensional sensing system that embodies the present invention (the first embodiment) will be described in detail hereafter based on FIGS. 1 to 8.

Figure 1:
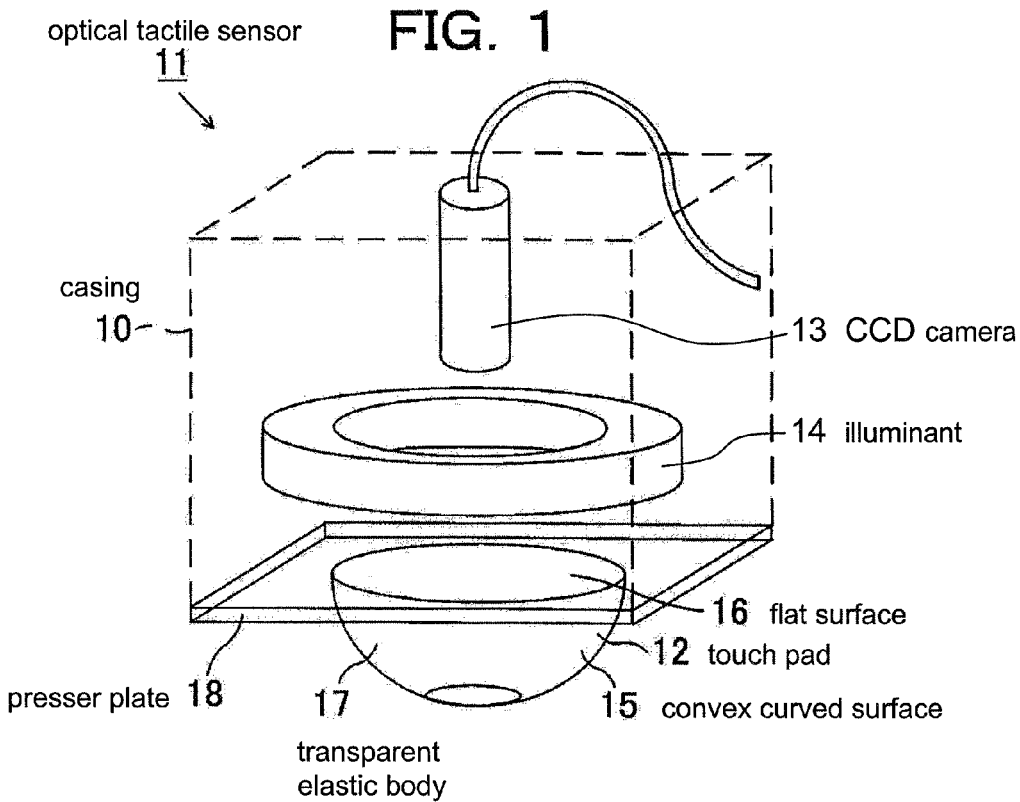
FIG. 1 is a perspective general view showing an optical tactile sensor according to the present invention.
Figure 2:
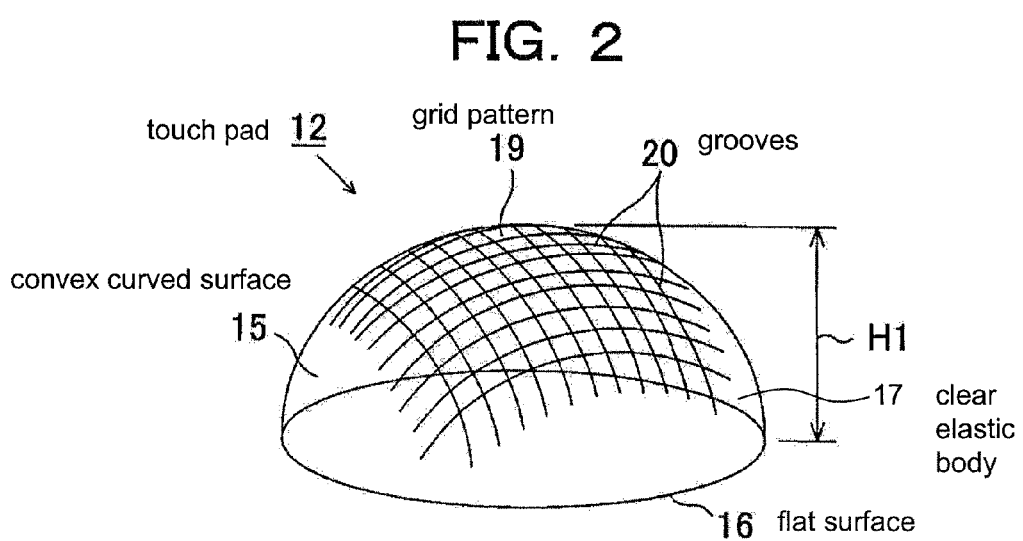
FIG. 2 is a perspective general view of a touch pad.

As shown in FIGS. 1 and 2, a cylindrical casing 10 encasing an optical tactile sensor 11 includes a tactile portion, such as touch pad 12 mounted on a distal end thereof. Disposed within the casing 10 is an imaging means, such as a CCD camera 13. The CCD camera 13 is disposed on the side of the touch pad 12 opposite to the side that makes contact with an object, W1 (see FIG. 3). The CCD camera 13 images the behavior (such as the displacement and deformation) of the grid pattern 19 on the touch pad 12 from behind while the object W1 is in touch with the touch pad 12. Accordingly, the CCD camera 13 is focused on the convex curved surface 15 of the touch pad 12, which bears the grid pattern 19.

Additionally disposed within the casing 10 is a circular illuminant 14 for illuminating the grid pattern 19. According to this embodiment, the illuminant 14 includes a plurality of light emitting diodes; however, the illuminant 14 may include other devices, such as optical fibers. The touch pad 12, the CCD camera 13, and the illuminant 14 are all disposed on the same axis.

As shown in FIG. 1, the touch pad 12 comprises a clear elastic body (optically transparent elastic body) 17 having the convex curved surface 15 on its distal end and a flat surface 16 on its proximal end. Bonded to the proximal end of the clear elastic body 17 with a transparent adhesive is a presser plate (presser member) 18 that is harder than the transparent elastic body 17. The presser plate 18 is also bonded to one end of the casing 10. According to this embodiment, a clear acrylic plate is used as the presser plate 18. The aforementioned CCD camera 13 is disposed on the side of the presser plate 18 opposite the side to which the touch pad 12 is bonded. According to this embodiment, the clear elastic body 17 is made of a clear silicone rubber (product No. YE5822 manufactured by GE Toshiba Silicones Co., LTD.). The clear elastic body 17 is sized to have a height (H1) of 13 mm and the convex curved surface 15 of the transparent elastic body 17 is adapted to have a radius of curvature of 20-30 mm 30 mm in this embodiment).

As shown in FIG. 2, the grid pattern 19 is arranged as a maker portion on the surface of the touch pad 12 that makes contact with the object W1 (see FIG. 3), i.e., on the convex curved surface 15. The grid pattern 19 is displaced and/or distorted when the clear elastic body 17 comes into contact with the object W1. More particularly, the grid pattern 19 is comprised of a plurality of grooves 20 arranged in a lattice. In this embodiment, the grid pattern 19 consists of a plurality of grooves having a depth of 100 micrometers arranged in a grid pattern with a 300-micrometer pitch. Accordingly, the grid pattern 19 is formed of the same material as the clear elastic body 17. Alternatively, each groove 20 may have a depth of 50 micrometers. In this embodiment, the grid pattern 19 is made of the same material as the clear elastic body 17; however, the grid pattern may be formed with a different material than the transparent elastic body 17.

This touch pad 12 is manufactured by casting uncured clear silicone rubber (an elastic body material) into a metal mold (not shown) having an approximately hemispherical molding surface, and allowing part of the transparent silicone rubber to be cured while in contact with the molding surface. In addition, the molding surface is provided with a plurality of molding ridges having a 100-micrometer height in a grid pattern. Accordingly, when the molding of the touch pad 12 is completed, this process provides the convex curved surface 15 of the clear elastic body 17 with a plurality of grooves 20 arranged in a grid pattern.

Figure 3:
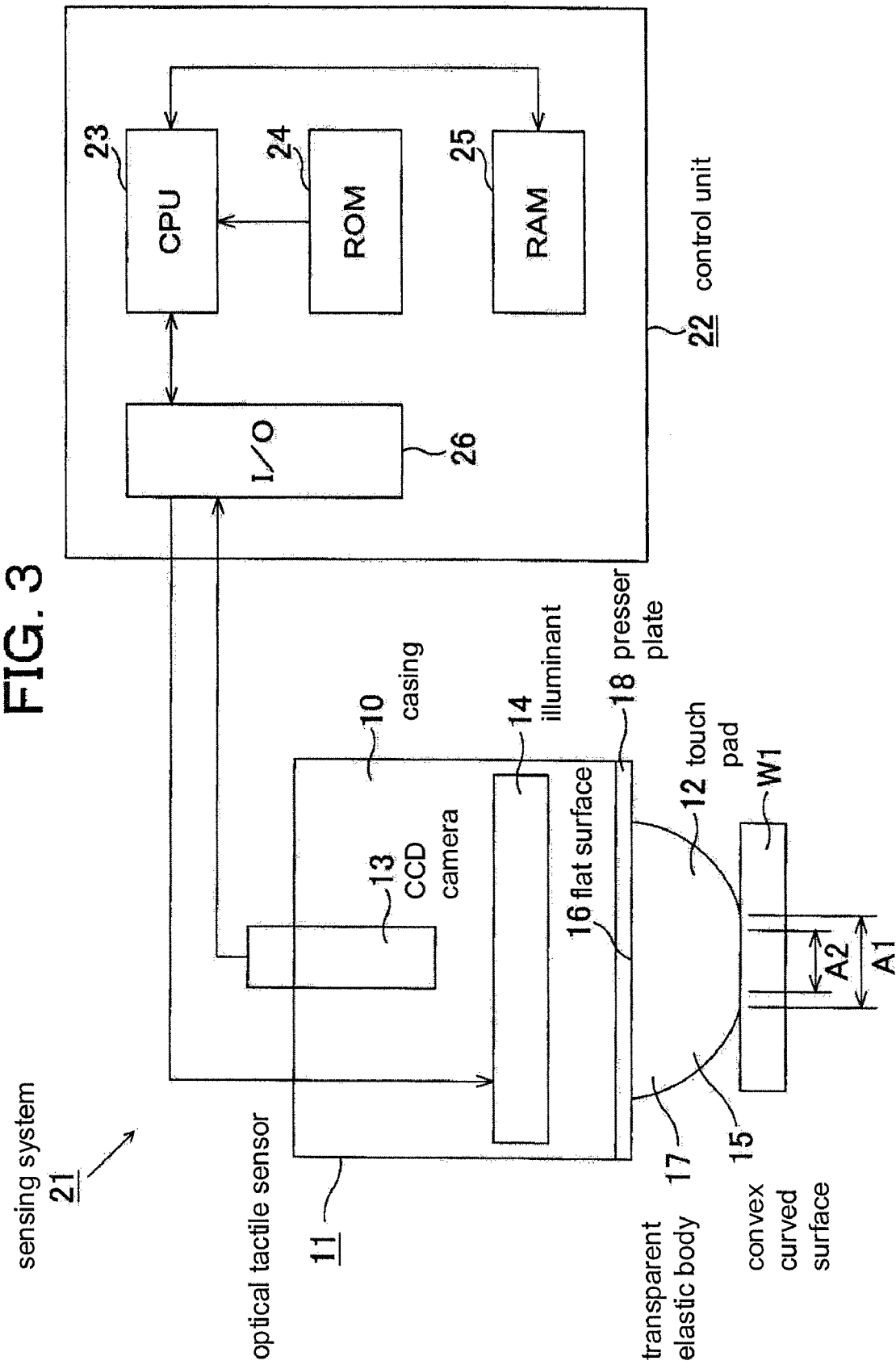
FIG. 3 is a block diagram showing the configuration of a sensing system.
Figure 4:
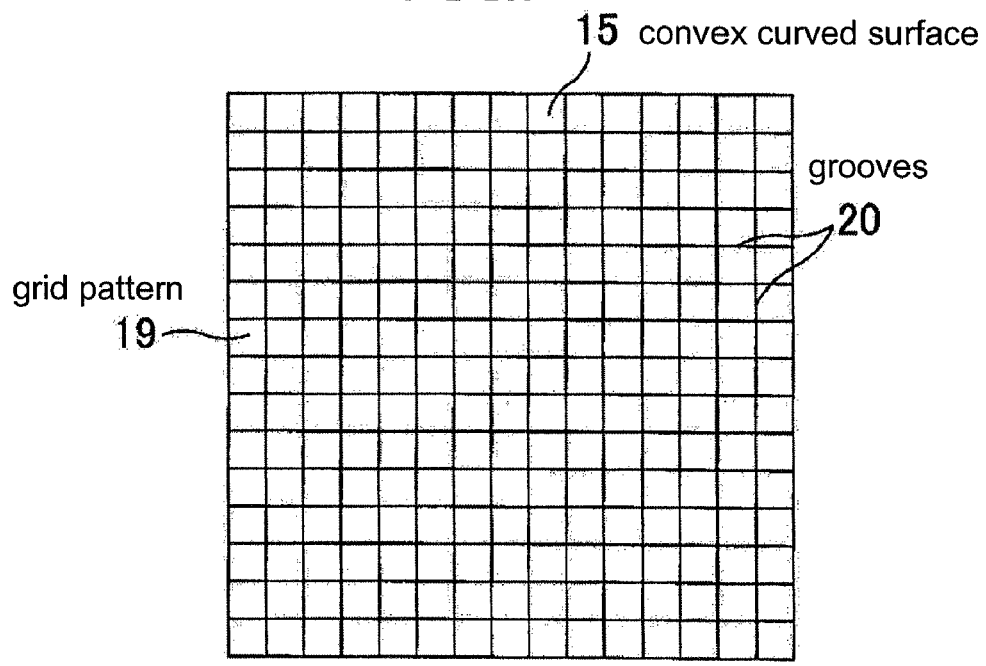
FIG. 4 shows a grid pattern when the touch pad is not in contact with any object.
Figure 5:
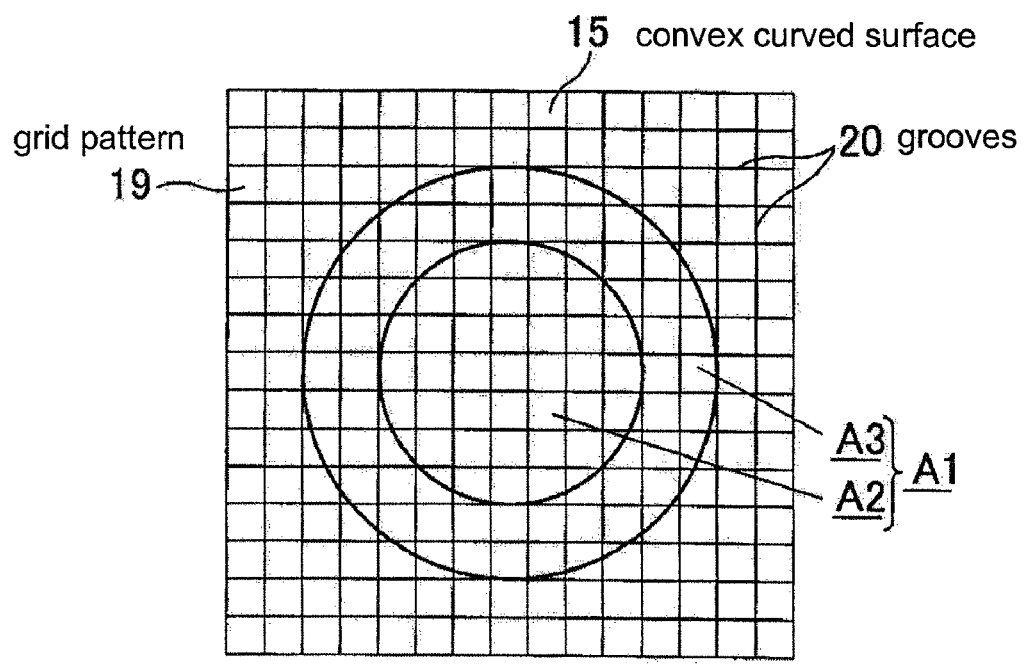
FIG. 5 shows the grid pattern when the touch pad is in contact with an object.
Figure 6:
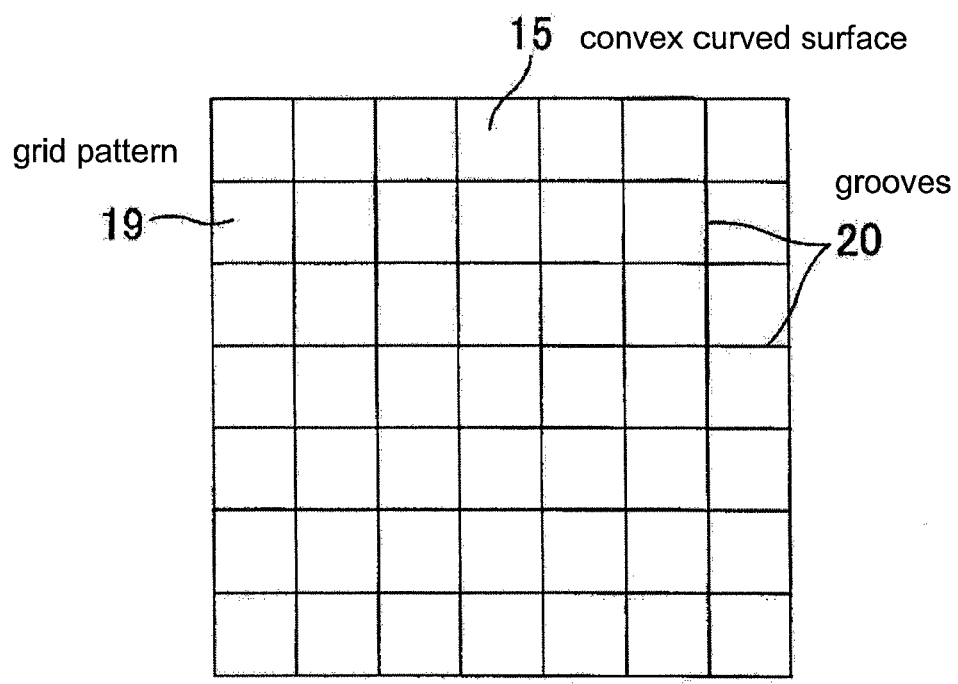
FIG. 6 shows the grid pattern when no torque is acting on the touch pad.
Figure 7:
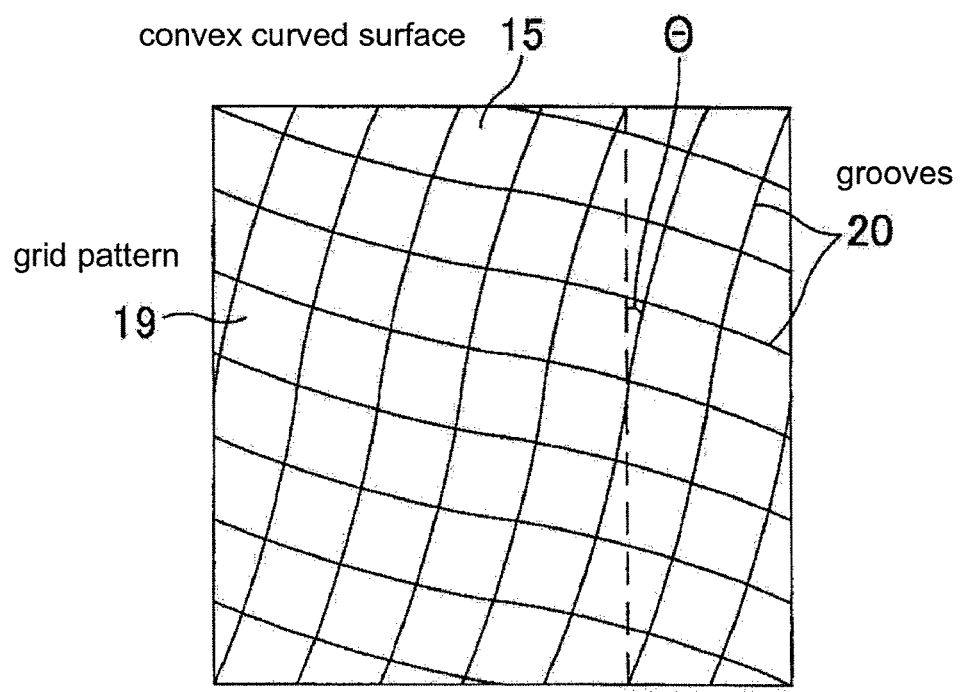
FIG. 7 shows the grid pattern when torque is acting on the touch pad.

FIG. 3 illustrates that the sensing system 21, which has an optical tactile sensor 11, includes a control unit 22 for controlling the overall operation of the sensing system 21. The control unit 22 has a CPU 23 to which a ROM 24, a RAM 25, and an input/output port (I/O port) 26 are connected. The CPU 23 performs various processes to control the overall operation of the sensing system 21 and generates the results of the processes as control signals in predetermined formats. The ROM 24 holds therein programs, such as those for controlling the operation of the sensing system 21. The RAM 25 temporarily stores various kinds of information necessary for the operation of the sensing system 21. In addition, the aforementioned CCD camera 13 and illuminant 14 are coupled to the input/output port 26. The image data on the behavior of the grid pattern 19 imaged and captured by the CCD camera 13 is output to the CPU 23 via the input/output port 26. Concurrently with the above, the CPU 23 sends the signal for turning on the illuminant 14 to the illuminant 14 via the input/output port 26.

The CPU 23, which is shown in FIG. 3, performs image processing of the image data received from the CCD camera 12 via the input/output port 26 at regular intervals (every 33 ms in this embodiment). This permits recognition of the grid pattern 19 as a lattice (see FIG. 4). The image data, captured at regular intervals, is stored in the storage are of the RAM 25 for a period of time until erased, oldest first. In this embodiment, a commercially available software program (product designation: HALCON available from MVTec Software GmbH) is used for the image processing. As the touch pad 12 comes into contact with the object W1, the CPU 23 extracts information about the size (area), the shape, and the center of gravity of the contact region A1 (see FIG. 5) that occurs between the object W1 and the touch pad 12 (i.e., geometrical data on the contact region A1). In addition, the CPU 23 extracts information about the size (area), the shape of a fixed region A2 (see FIG. 5) between the object W1 and the touch pad 12 that occurs within the contact region A1 (i.e., geometrical data on the fixed region). This means that the CPU 23 functions as a data or information extractor. As used herein, the term "fixed region A2" refers to the portion of the grid pattern 19 that remains stationary while the touch pad 12 is in contact with the object W1. As used herein, the portion of the grid pattern 19 that shifts while the touch pad 12 is in contact with the object W1 is referred to as a slipping region A3 (see FIG. 5).

The following describes a method for determining the fixed region A2, the slipping region A3, and the contact region A1:

In the image of the touch pad 12 in contact with the object W1 photographed by the CCD camera 13 (see FIG. 5), the grid pattern 19 may be recognized as a lattice with the contact region A1 appearing brighter than the remaining area. This means that the area of the contact region A1 may be measured based on the differences in luminance on the image. This embodiment employs as the illuminant 14 a lighting device that emits white light for illuminating the grid pattern 19 as white light creates a large difference in luminance between the contact region A1 and the area not in contact with the object. This provides for shaper recognition of the contact region A1.

Next, the image photographed in the previous step (33 ms earlier) is subtracted from the current image in order to increase its contrast by modifying the image. This allows the slipping region A3 (where the grid pattern 19 shifts) to be displayed in a lattice. In contrast, the fixed region A2 appears as a blurred, white-noise image without displaying a lattice. This results in a well-defined delimitation between the fixed region A2 and the slipping region A3, thus allowing clear determination of the border between the two areas based on the image. The foregoing processing enables separate measurements of the fixed region A2 and the slipping region A3

The CPU 23, illustrated in FIG. 3, determines the coefficient of friction (i.e., slip) between the object W1 and the clear elastic body 17 based on the ratio of the area of the fixed region A2 to that of the contact region A1. Specifically, the CPU 23, for example, reads from the aforementioned ROM 24 the data that indicates the relationship between the coefficient of friction and the ratio of the area of the fixed region A2 to that of the contact region A1. The CPU 23 then selects the data indicating the coefficient of friction that corresponds to the measured ratio of the size of the fixed region A2 to that of the contact region A1. This selection determines the coefficient of friction approximately on the contact region A1. It should be noted that as the ratio of the size of the fixed region A2 to that of the contact region A1 becomes greater, the slipping region A3 becomes smaller, thus increasing the coefficient of friction between the two objects. Alternatively, the coefficient of friction may be obtained by a method other than the above.

Additionally, the CPU 23 obtains a normal force from the size of the contact region A1. The term "normal force," as used herein, refers to the force acting on the object W1 in the vertical direction that occurs when the aforementioned clear elastic body 17 of the touch pad 12 presses against the object W1. More particularly, for example, the CPU 23 retrieves from the ROM 24 data that indicates the relationship between the size of the contact region A1 and the normal force. The CPU 23 then determines the magnitude and the direction of the normal force acting approximately on the contact region A1 by selecting the data representing the normal force that corresponds to the measured size of the contact region A1. Alternatively, the normal force may be obtained by a method other than the above. This means that the CPU 23 functions as a means for measuring mechanical quantities.

Furthermore, the CPU 23, shown in FIG. 3, obtains a tangential force from the shape and the center of gravity of the contact region A1. The term "tangential force," as used herein, refers to the force acting on the object W1 in the horizontal direction that occurs when the aforementioned clear elastic body 17 presses against the object W1. More particularly, the CPU 23, for example, retrieves from the ROM 24 data indicating the relationship between the tangential force and the shape and the center of gravity of the contact region A1. The CPU 23 then determines the magnitude and the direction of the tangential force acting approximately on the contact region A1 by selecting the data indicating the tangential force that corresponds to the measured shape and the center of gravity of the contact region A1. Alternatively, the tangential force may be obtained by a method other than the above.

The CPU 23 additionally extracts information about the deformation of the grid pattern 19 by image processing the image data received from the aforementioned CCD camera 13. The CPU 23 then obtains a torque from the deformation of the grid pattern 19. More particularly, for example, the CPU 23 compares an image of the grid pattern 19 before its deformation (before the elastic body comes into contact with the object W1), shown in FIG. 6, with an image of the grid pattern 19 after its deformation (after the elastic body comes into contact with the object W1), shown in FIG. 7, so as to measure the torsion of the lattice (the angle θ). Next, the CPU 23 retrieves from the ROM 24 data representing the relationship between the angle θ and the torque. The CPU 23 then determines the magnitude and the direction of the torque acting approximately on the contact region A1 by selecting the data on the torque that corresponds to the measured angle θ. Alternatively, the torque may be obtained by a method other than the above.

Figure 8:
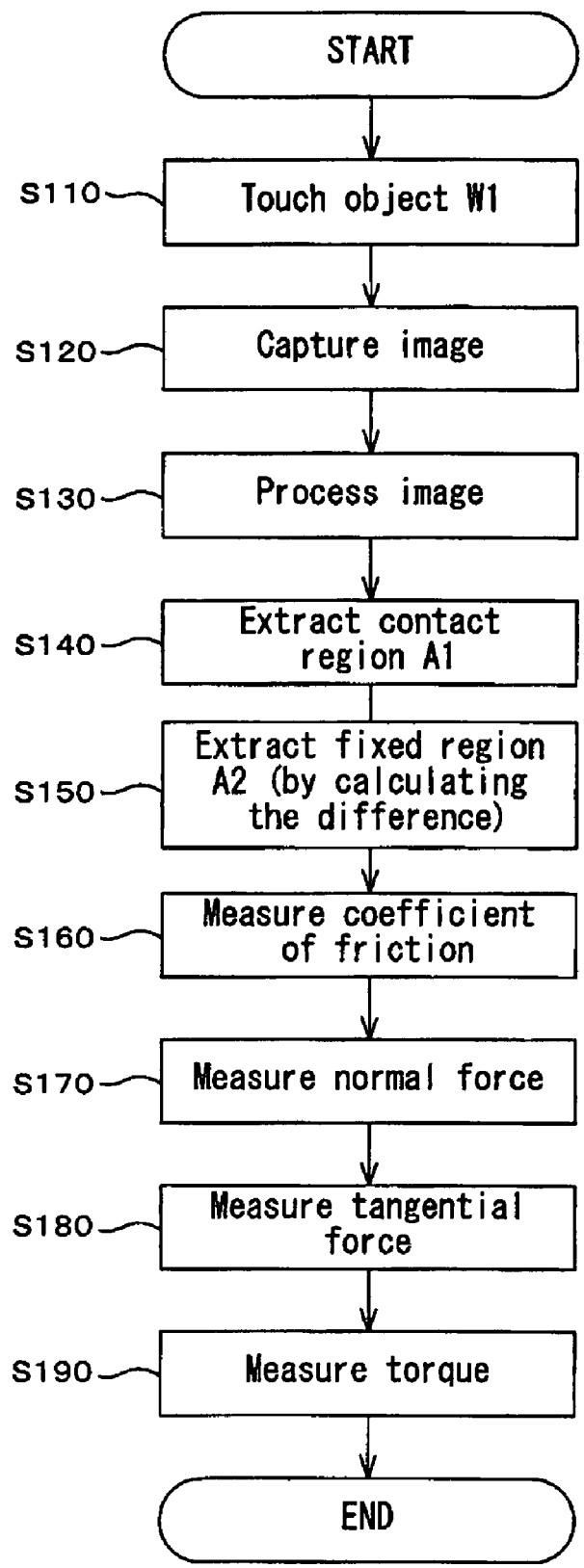
FIG. 8 is a flowchart schematically representing the processing performed by the sensing system.

The following describes the method employed by the sensing system 21 to measure the mechanical quantities (the normal force, the tangential force, the coefficient of friction, and the torque):

As shown in FIG. 8, when the touch pad 12 comes into contact with the object W1 in Step S110, the CPU 23 captures the image data received from the CCD camera 13 that has been obtained by the camera 13 imaging the behavior of the grid pattern 19 (Step S120) and then performs image processing on the data (Step S130). Subsequently, the CPU 23 carries out measurements of the contact region A1 based on the difference in luminance between the contact region A1 and the non-contact region so as to extract information about the size, shape, and center of gravity of the contact region A1 (Step S140). Next, the CPU 23 subtracts the immediately preceding image (33 ms earlier) from the current image. The CPU 23 also performs measurements of the fixed region A2 from the white-noise image obtained by modifying the image for an increased contrast. Moreover, the CPU 23 extracts information about the size of the fixed region A2 based on the result of the measurements (Step S150).

The CPU 23 then calculates the coefficient of friction between the object W1 and the clear elastic body 17 based on the ratio of the size of the fixed region A2 to that of the contact region A1 (Step S160). The CPU 23 continues to obtain the normal force from the size of the contact region A1 (Step S170) and the tangential force based on the shape and the center of gravity of the contact region A1 (Step S180). The CPU 23 further obtains the torsional torque (the angle θ) of the grid pattern 19 (Step S190) and the process is terminated at this point. The sequence of the processes of Steps S160 to S190 may be changed.

Accordingly, this embodiment produces the following effects:

Since the optical tactile sensor 11 captures the behavior of the clear elastic body 17 as image data through the use of the CCD camera 13, a large amount of information can be processed with a relatively small and simple structure. Accordingly, even different types of mechanical quantities (a normal force, a tangential force, a friction coefficient, and a torque) can be measured simultaneously without using a combination of different types of sensors. This provides for easy manufacture of a small, low-cost optical tactile sensor 11. Furthermore, the optical tactile sensor 11 largely has no problems in regards to durability, since mechanical quantities are not measured by causing deformation of strain gauges, as is conventional. Moreover, the grid pattern 19 or a plurality of strain gauges need not be disposed or arranged inside the clear elastic body 17; all that is required is to arrange the grid pattern 19 on the convex curved surface 15. Moreover, the basic components constituting the optical tactile sensor 11 (the clear elastic body 17, the illuminant 14, and the CCD camera 13) are relatively few. This provides for easy manufacture of the optical tactile sensor 11.

The convex curved surface 15 is the part of the touch pad 12 most susceptible to deformation when the pad 12 comes into contact with the object W1. The amount of deformation progressively decreases from the convex curved surface 15 into the inside of the touch pad 12. Therefore, the grid pattern 19 of this embodiment, being arranged on the convex curved surface 15, tends to exhibit greater deformation compared with a grid pattern 19 formed within the touch pad 12. This allows for accurate determination of the forces acting on the touch pad 12 when the CCD camera 13 images the deformation of the grid pattern 19. In other words, this embodiment can measure the deformation of the clear elastic body 17 more accurately than the method for measuring the deformation that occurs inside the elastic body.

According to the sensing system 21 of this embodiment, once image data received from the CCD camera 13 is image processed, the CPU 23 extracts information about the size, shape, and center of gravity of the contact region A1 as well as the size of the fixed region A2. The CPU 23 then obtains the normal force, the tangential force, the coefficient of friction, and the torque based on that information. In other words, one type of sensor simultaneously measures different types of mechanical quantities in an exemplary embodiment.

According to this embodiment, the grid pattern 19, which is disposed on the convex curved surface 15, consists of a lattice of grooves 20. This forms asperities on the convex curved surface 15.

This in turn produces increased mechanical engagement between the grid pattern 19 and the surface of the object W1 when the clear elastic body 17 is in contact with the object W1, thus increasing the coefficient of friction about the area of the convex curved surface 19 where the grid pattern 19 is located. Accordingly, this augments the "grip" of the touch pad 12 on the object W1.

According to this embodiment, the proximal end of the clear elastic body 17 is formed flat (the flat surface 16), and the presser plate 18 is bonded thereon. As this arrangement prevents deformation of the proximal portion of the clear elastic body 17, the optical tactile sensor 11 can measure mechanical quantities with enhanced accuracy.

In addition, the presser plate 18 facilitates stable support of the touch pad 12. Thus stably supported, the touch pad 12 in turn facilitates imaging of the grid pattern 19 by the CCD camera 13.

The second embodiment will now be described with reference to FIGS. 9 and 10. It should be noted that the components and members of this embodiment that are also used in first embodiment are assigned the same reference numbers and that detailed description thereof is omitted.

In the first embodiment, the optical tactile sensor 11 is employed in the sensing system 21. In this embodiment, the optical tactile sensor 11 is used in a robot hand 31 (an apparatus for controlling object operating force and for controlling object gripping force).

Figure 9:
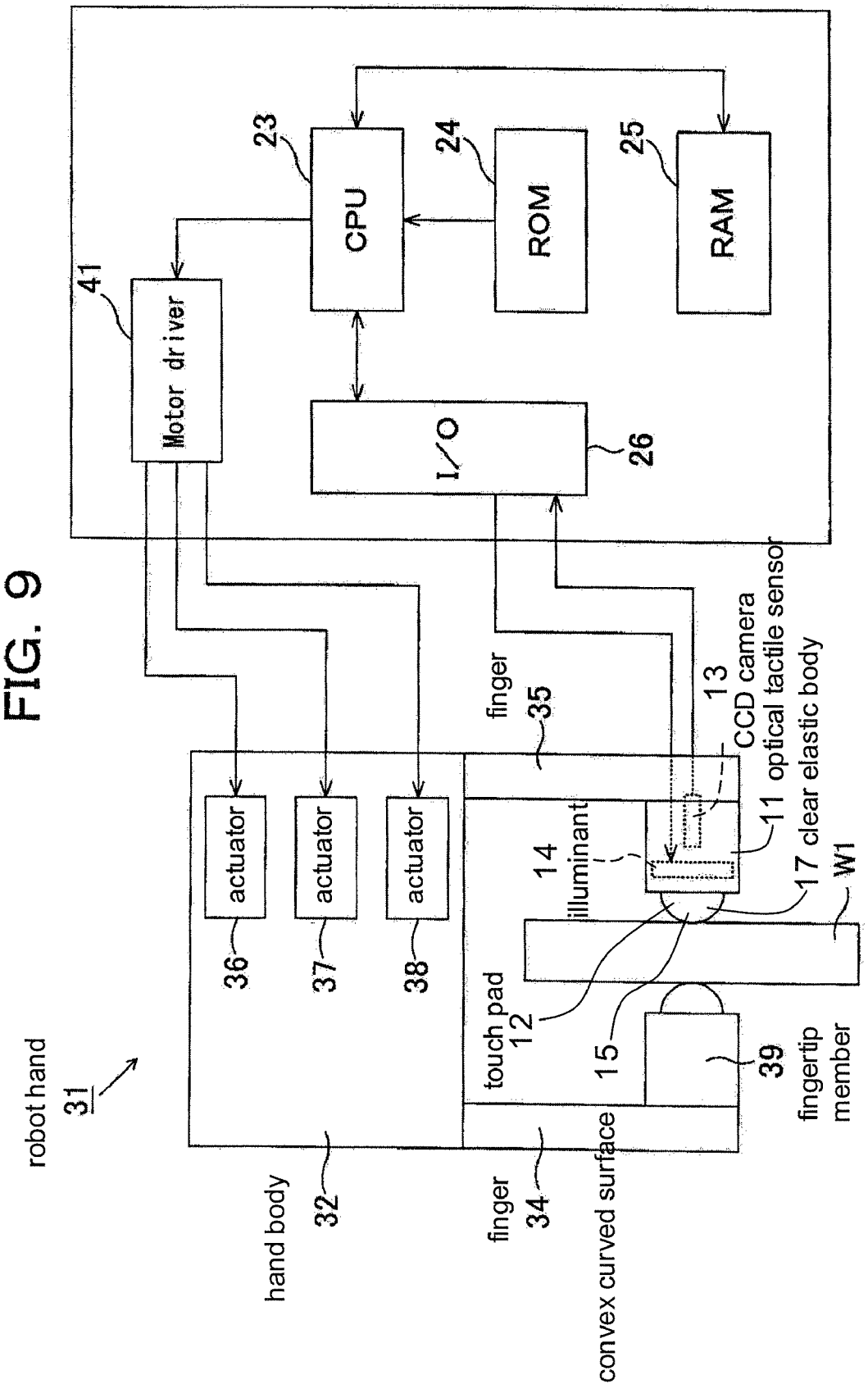
FIG. 9 is a block diagram showing the configuration of a robot hand.
Figure 10:
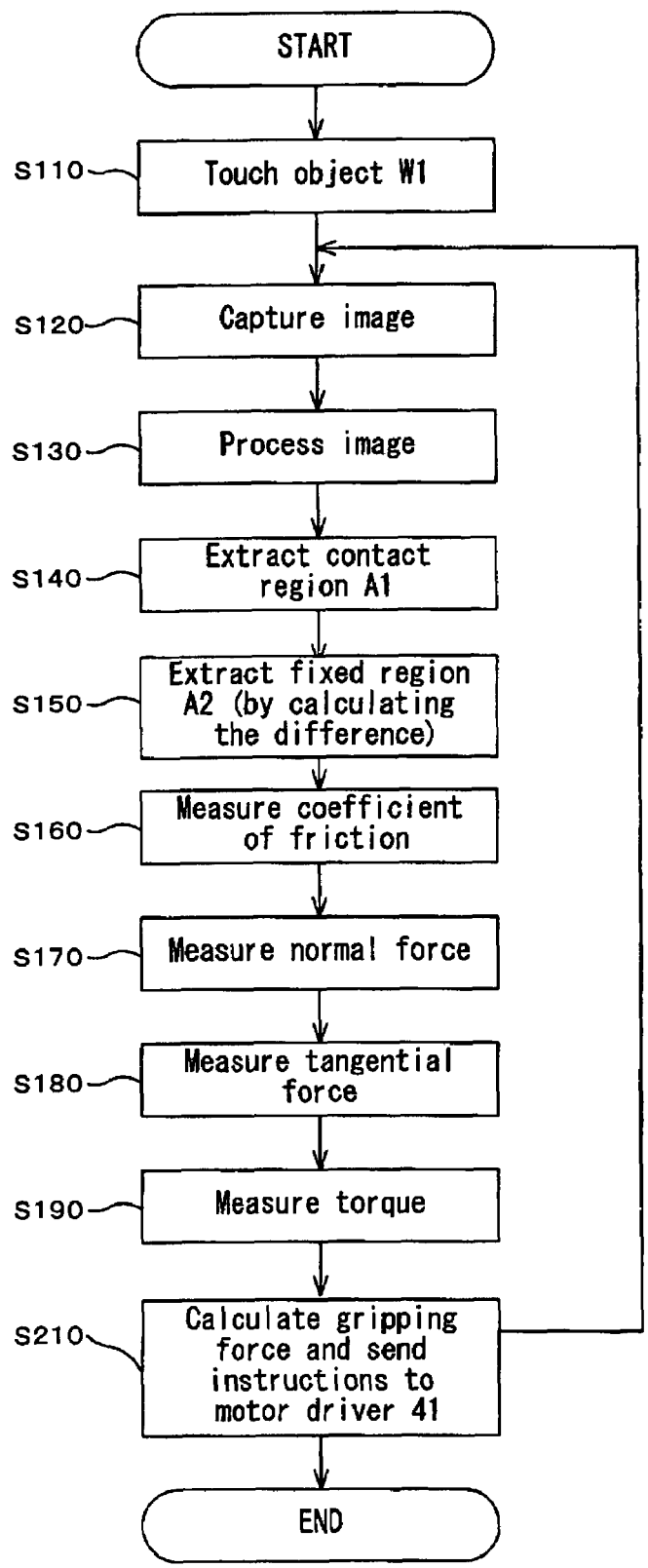
FIG. 10 is a flowchart schematically representing the processing performed by the robot hand.

As shown in FIG. 9, the hand body 32, which constitutes the main part of the robot hand 31, includes a pair of fingers (sensor supports) 34 and 35. According to this embodiment, the two fingers 34 and 35 are provided on the hand body 32. However, two or more fingers (34, 35) may be provided; for example, five fingers may be employed as on a human hand. Additionally, the hand body 32 includes a first servomotor 36 (actuator), a second servomotor 37 (actuator), and a third servomotor 38 (actuator). The fingers 34 and 35 are driven by the first servomotor 36 to open and close (i.e., in the right-left directions in FIG. 9). The fingers 34 and 35 are driven by the second servomotor 37 to move in directions orthogonal to those in which the fingers 34 and 35 open and close and in the horizontal directions (i.e., the forward-and-backward directions in FIG. 9). Furthermore, the third servomotor 38 drives the fingers 34 and 35 to move in the vertical directions (i.e., the upward and downward directions in FIG. 9).

As shown in FIG. 9, one of the fingers—the finger 35—includes the optical tactile sensor 11 supported thereon. The other finger 34 includes a fingertip member 39 supported thereon that has approximately the same external shape as the optical tactile sensor 11. The fingertip member 39 and the optical tactile sensor 11 are arranged to oppose each other. Alternatively, another optical tactile sensor 11 may be mounted in place of the fingertip member 39. In other words, an optical tactile sensor 11 may be mounted on one or both of the fingers 34 and 35.

The control unit 22, which is responsible for controlling the overall operation of the robot hand 31, includes a motor driver 41 for driving the servomotors 36 to 38 and controlling the position and speed of and the force exerted by the fingers 34 and 35. The CPU 23 controls the operation of the motor drivers 41. The motor driver 41 supplies electrical currents having predetermined waveforms to the servomotors 36 to 38 based on driving signals generated by the CPU 23.

The CPU 23, shown in FIG. 9, calculates the amounts and directions of the gripping force (operating force) suitable for application to the object W1, based on the normal force, the tangential force, the coefficient of friction, and the torque obtained by the CPU 23. For example, if it is possible that application to the object W1 of a normal force in excess will result in damage to the object W1, the CPU 23 reduces the normal force (the forces of the fingers 34 and 35 to close as they are driven by the first servomotor 36). Conversely, if it is a possibility that insufficient normal forces will be applied to the object W1, the CPU 23 is adapted to increase the normal forces to prevent the object from slipping through the fingers. This means that the CPU 23 functions as a means for calculating mechanical operating force and gripping force. Additionally, based on the appropriate gripping forces thus calculated, the CPU 23 instructs the motor driver 41 to drive the first, second, and third servomotors 36 to 38. These instructions cause the fingers 34 and 35 to grip the object W1 with appropriate gripping forces. In this way, the CPU 23 performs feedback control of the gripping forces. This means that the CPU 23 also functions as a means for controlling the drive of the actuators.

The following describes the method by which the robot hand 31 grips the object W1: In FIG. 10, once the process from Step S110 to Step S190 is completed to measure the normal force, the tangential force, the coefficient of friction, and the torque, the CPU 23 proceeds to Step S210. In Step S210, the CPU 23 calculates a gripping force suitable for application to the object W1, based on the obtained normal force, tangential force, coefficient of friction, and torque. Then, the CPU 23 instructs the motor driver 41 to drive the first, second, and third servomotors 36 to 38 with the calculated appropriate gripping force. These instructions causes the fingers 34 and 35 to grip the object W1 with an appropriate gripping force.

Upon completing the process of Step S210, the CPU 23 iterates the process of Step S120 to Step S210. This process is carried out at regular intervals while the fingers 34 and 35 are gripping the object W1. This means that the CPU 23 performs feedback control of the gripping force.

Accordingly, this embodiment produces the following effects:

According to the robot hand 31 of this embodiment, once image data received from the CCD camera 13 is image processed, the CPU 23 extracts information about the size, shape, and center of gravity of the contact region A1 as well as the size of the fixed region A2. The CPU 23 then obtains the normal force, the tangential force, the coefficient of friction, and the torque based on that information.

In other words, a single type of sensor may simultaneously measure different types of mechanical quantities. A gripping force suitable for application to the object W1 may then be calculated based on the measured mechanical quantities.

This permits the fingers 34 and 35 to grip the object W1 without damaging or allowing it to slip. Moreover, in an exemplary embodiment, the touch pad 12 of the optical tactile sensor 11, having a hemispherical shape, grips the object W1 irrespective of the shape of the object. This facilitates the creation of a humanoid robot with the robot hand 31 having functionality closer to that of the human hand.

In this embodiment, even if the appropriate operating force to be exerted on the object W1 changes during the operation, the object W1 can continue to be securely gripped using the feedback operation performed by the CPU 23 without being damaged or slipping. In addition, since the optical tactile sensor 11 captures the behavior of the clear elastic body 17 as image data through the use of the CCD camera 13, a large amount of information can be processed relatively fast. Accordingly, even if the appropriate operating force to be exerted on the object W1 suddenly changes while it is gripped, the object W1 can continue to be securely gripped without being damaged or slipping.

The embodiments of the present invention may be modified as follows:

Although the pattern 19 is in a grid in the foregoing embodiments, it may be selected from other patterns, such as a triangular mesh and hexagonal mesh (a honeycomb pattern).

In the foregoing embodiments, the grid pattern 19 may be coated with a cover layer of an optically transparent material.

As described above, in the foregoing embodiments, as the touch pad 12 is formed in a shaping mold, a plurality of grooves 20 is formed on the convex curved surface 15 of the clear elastic body 17. Alternatively, the grooves 20 may be formed after the fabrication of the touch pad 12, for example, by cutting.

In the foregoing embodiment, the illuminant 14 emits white light. Alternatively, the illuminant 14 may be adapted to emit blue, red, or other light.

The second embodiment employs the first, second, and third servomotor 36 to 38 as the actuators to drive the fingers 34 and 35. Alternatively, other types of actuators, such as hydraulic cylinders, pneumatic cylinders, and ultrasonic motors, may be used instead.

An optical tactile sensor and a sensing system incorporating the optical tactile sensor according to the present invention may facilitate two-way communication of tactile information between humans and robots. For example, the present invention may be applicable to robot teaching machines which, in exemplary embodiments, teach robots subtle movements and sensitivity required of fingertips in, for example, throwing a ball.

What is claimed is:

1. An optical tactile sensor, comprising,
   a tactile portion made of an optically transparent elastic body which includes a convex curved surface on a distal end thereof and a flat surface on a proximal end thereof and has a marker portion disposed on the convex curved surface, the tactile portion being disposed on an axis;
   a presser member which is harder than the optically transparent elastic body and bonded to the distal end of the optically transparent elastic body;
   imaging means disposed behind the tactile portion via the presser member for imaging behavior of the marker portion from behind the tactile portion while an object is in contact with the convex curved surface; and a circular illuminant disposed on the axis for illuminating the marker portion.

2. An optical tactile sensor in accordance with claim 1, wherein the marker portion includes a plurality of grooves or ridges arranged in a grid pattern.

3. An optical tactile sensor in accordance with claim 1, wherein the tactile portion is formed by providing a mold having a molding surface including a plurality of molding grooves or ridges on the molding surface and allowing material for an elastic body in an uncured state to be cured while in contact with the molding surface.

4. An optical tactile sensor in accordance with claim 1, wherein the marker portion comprises a plurality of grooves having a depth of 100-1000 micrometers arranged in a grid pattern with a 300-1000 micrometer pitch.

5. A method for sensing different types of mechanical quantities by using an optical tactile sensor that has a tactile portion made of an optically transparent elastic body and imaging means for imaging behavior of a part of the tactile portion with which an object comes into contact, the method comprising the steps of:

extracting information on the size, shape, and center of gravity of a contact region that occurs between the object and the tactile portion, and extracting information on the size of a fixed region between the object and the tactile portion that occurs within the contact region, both by processing image data from the imaging means;

determining a normal force based on a relationship between the size of the contact region and the normal force;

determining a tangential force based on a relationship between the tangential force and the shape and the center of gravity of the contact region; and obtaining a coefficient of friction from the ratio of the size of the fixed region to the size of the contact region.

6. A sensing system, comprising:

an optical tactile sensor that has a tactile portion made of an optically transparent elastic body and imaging means for imaging behavior of a part of the tactile portion with which an object comes into contact;

means for extracting information on the size, shape, and center of gravity of a contact region that occurs between the object and the tactile portion and for extracting information on the size of a fixed region between the object and the tactile portion that occurs within the contact region, both by processing image data from the imaging means; and mechanical quantity measuring means for determining a normal force based on a relationship between the size of the contact region and the normal force, determining a tangential force based on a relationship between the tangential force and the shape and the center of gravity of the contact region, and obtaining a coefficient of friction from the ratio of the size of the fixed region to the size of the contact region.

7. A sensing system according to claim 6, further comprising:

a marker portion is disposed on the part of the tactile portion with which the object comes into contact with, wherein:

the imaging means images behavior of the marker portion while the object is in contact with the tactile portion;

the information extraction means extracts information about a deformation of the marker portion by image processing the image data from the imaging means; and the mechanical quantity measuring means is provided for obtaining a torque from the deformation of the marker portion.

8. A method for controlling forces for operating an object by using an optical tactile sensor that has a tactile portion made of an optically transparent elastic body and imaging means for imaging behavior of a part of the tactile portion with which an object comes into contact, the method comprising the steps of:

extracting information on the size, shape, and center of gravity of a contact region that occurs between the object and the tactile portion, and extracting information on the size of a fixed region between the object and the tactile portion that occurs within the contact region, both by processing image data from the imaging means;

determining a normal force based on a relationship between the size of the contact region, and the normal force, determining a tangential force based on a relationship between the tangential force and the shape and the center of gravity of the contact region, and obtaining a coefficient of friction from the ratio of the size of the fixed region to the size of the contact region;

calculating an operating force for application to the object based on the normal force, the tangential force or the coefficient of friction; and controlling the normal force or the tangential force to approximate the normal force or the tangential force to the calculated operating force.

9. An apparatus for controlling forces to operate an object, comprising:

a sensor support;

an actuator for driving the sensor support;

an optical tactile sensor that has a tactile portion made of an optically transparent elastic body and imaging means for imaging behavior of a part of the tactile portion that comes into contact with an object, the optical tactile sensor being supported by the sensor support;

information extracting means for extracting information on the size, shape, and center of gravity of a contact region that occurs between the object and the tactile portion and for extracting information on the size of a fixed region between the object and the tactile portion that occurs within the contact region, both by processing image data from the imaging means;

mechanical quantity measuring means for determining a normal force based on a relationship between the size of the contact region and the normal force, determining a tangential force based on a relationship between the tangential force and the shape and the center of gravity of the contact region, and obtaining a coefficient of friction from the ratio of the size of the fixed region to the size of the contact region;

operating force calculating means for calculating an operating force for application to the object based on the normal force, the tangential force or the coefficient of friction; and actuator drive control means for performing feedback control of the actuator so as to drive the sensor support with the operating force calculated by the operating force calculating means.

10. An apparatus for controlling forces to grip an object, comprising:

a sensor support;

an actuator for driving the sensor support;

an optical tactile sensor that has a tactile portion made of an optically transparent elastic body and imaging means for imaging behavior of a part of the tactile portion that comes into contact with an object, the optical tactile sensor being supported by the sensor support;

information extracting means for extracting information on the size, shape, and center of gravity of a contact region that occurs between the object and the tactile portion and for extracting information on the size of a fixed region between the object and the tactile portion that occurs within the contact region, both by processing image data from the imaging means;

mechanical quantity measuring means for determining a normal force based on a relationship between the size of the contact region and the normal force, determining a tangential force based on a relationship between the tangential force and the shape and the center of gravity of the contact region, and obtaining a coefficient of friction from the ratio of the size of the fixed region to the size of the contact region;

gripping force calculating means for calculating a gripping force for application to the object based on the normal force, the tangential force or the coefficient of friction; and actuator drive control means for performing feedback control of the actuator so as to drive the sensor support with the gripping force calculated by the gripping force calculating means.

11. A robot hand, comprising:

a plurality of fingers;

actuators for driving the plurality of fingers;

at least one optical tactile sensor that has a tactile portion made of an optically transparent elastic body and imaging means for imaging behavior of a part of the tactile portion that comes into contact with an object, each of the at least one optical tactile sensor being supported by a distal end of one of the plurality of fingers;

information extracting means for extracting information on the size, shape, and center of gravity of a contact region that occurs between the object and the tactile portion and for extracting information on the size of a fixed region between the object and the tactile portion that occurs within the contact region, both by processing image data from the imaging means;

mechanical quantity measuring means for determining a normal force based on a relationship between the size of the contact region and the normal force, determining a tangential force based on a relationship between the tangential force and the shape and the center of gravity of the contact region, and obtaining a coefficient of friction from the ratio of the size of the fixed region to the size of the contact region;

gripping force calculating means for calculating a gripping force for application to the object based on the normal force, the tangential force or the coefficient of friction; and actuator drive control means for performing feedback control of the actuators so as to drive the plurality of fingers with the gripping force calculated by the gripping force calculating means.

* * * * *